US009504852B2

(12) United States Patent
Fujisawa

(10) Patent No.: US 9,504,852 B2
(45) Date of Patent: Nov. 29, 2016

(54) MEDICAL IMAGE PROCESSING APPARATUS AND RADIATION TREATMENT APPARATUS

(71) Applicant: Toshiba Medical Systems Corporation, Otawara-shi (JP)

(72) Inventor: Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/632,789

(22) Filed: Feb. 26, 2015

(65) Prior Publication Data

US 2015/0165235 A1    Jun. 18, 2015

Related U.S. Application Data

(63) Continuation of application No. PCT/JP2013/073713, filed on Sep. 3, 2013.

(30) Foreign Application Priority Data

Sep. 3, 2012  (JP) ................................. 2012-193564
Sep. 3, 2013  (JP) ................................. 2013-182609

(51) Int. Cl.
*G06K 9/00*   (2006.01)
*A61B 6/00*   (2006.01)
(Continued)

(52) U.S. Cl.
CPC ............. *A61N 5/1039* (2013.01); *A61B 5/055* (2013.01); *A61B 5/7425* (2013.01);
(Continued)

(58) Field of Classification Search
CPC ............. A61B 6/00; A61N 5/00; G06T 7/00
USPC ....... 382/128, 129, 130, 131, 132, 133, 134; 378/4, 21–27, 901; 600/407, 410, 411, 600/425, 443
See application file for complete search history.

(56) References Cited

U.S. PATENT DOCUMENTS 6,473,634 B1 * 10/2002 Barni ....................... A61B 6/00
                                                                  382/131
9,220,468 B2 * 12/2015 Kitamura ........... A61B 1/00009

FOREIGN PATENT DOCUMENTS

JP    03-026242 A    2/1991
JP    08-024254 A    1/1996
(Continued)

OTHER PUBLICATIONS

International Search Report mailed Nov. 5, 2013 for PCT/JP2013/073713 filed on Sep. 3, 2013 with English Translation.
(Continued)

*Primary Examiner* — Abolfazl Tabatabai
(74) *Attorney, Agent, or Firm* — Oblon, McClelland, Maier & Neustadt, L.L.P.

(57) ABSTRACT

A medical image processing apparatus includes: an extracting unit that extracts a region of interest and a treatment target organ from each of pieces of three-dimensional medical image data acquired chronologically; a generating unit that generates a movable region image in which each of images of the region of interest that correspond to specified phases and that are among images of the region of interest extracted by the extracting unit from the pieces of three-dimensional medical image data is arranged in an extraction position in a three-dimensional coordinate system, while being characterized in such a manner that the phases are recognizable; and a display controlling unit that causes a display unit to display a display image in which the movable region image during a treatment is superimposed, in a coordinate-corresponding manner, on an image showing the treatment target organ and corresponding to phases during the treatment.

10 Claims, 10 Drawing Sheets

(51) Int. Cl.
| | |
|---|---|
| *A61N 5/10* | (2006.01) |
| *A61B 5/055* | (2006.01) |
| *A61B 5/00* | (2006.01) |
| *G06T 7/00* | (2006.01) |
| *G06T 7/20* | (2006.01) |
| *A61B 6/12* | (2006.01) |
| *G06T 19/00* | (2011.01) |
| *A61B 5/05* | (2006.01) |
| *A61B 6/03* | (2006.01) |
| *A61B 5/091* | (2006.01) |

(52) U.S. Cl.
CPC ............ *A61B 5/7485* (2013.01); *A61B 6/032* (2013.01); *A61B 6/12* (2013.01); *A61B 6/5217* (2013.01); *A61B 6/5288* (2013.01); *A61N 5/1037* (2013.01); *G06T 7/0012* (2013.01); *G06T 7/2006* (2013.01); *G06T 19/00* (2013.01); *A61B 5/091* (2013.01); *A61B 6/03* (2013.01); *A61B 6/463* (2013.01); *A61B 6/469* (2013.01); *A61B 6/504* (2013.01); *A61B 2576/02* (2013.01); *A61N 2005/1054* (2013.01); *G06T 2207/10012* (2013.01); *G06T 2207/10081* (2013.01); *G06T 2207/10088* (2013.01); *G06T 2210/41* (2013.01); *G06T 2219/008* (2013.01)

(56) References Cited

FOREIGN PATENT DOCUMENTS

| | | |
|---|---|---|
| JP | 08-089589 A | 4/1996 |
| JP | 2002-186678 A | 7/2002 |
| JP | 03-931792 B2 | 8/2003 |
| JP | 2004-513735 A | 5/2004 |
| JP | 2010-131315 A | 6/2010 |
| JP | 2012-085969 A | 5/2012 |

OTHER PUBLICATIONS

International Written Opinion mailed Nov. 5, 2013 for PCT/JP2013/073713 filed on Sep. 3, 2013.

\* cited by examiner

FIG.3
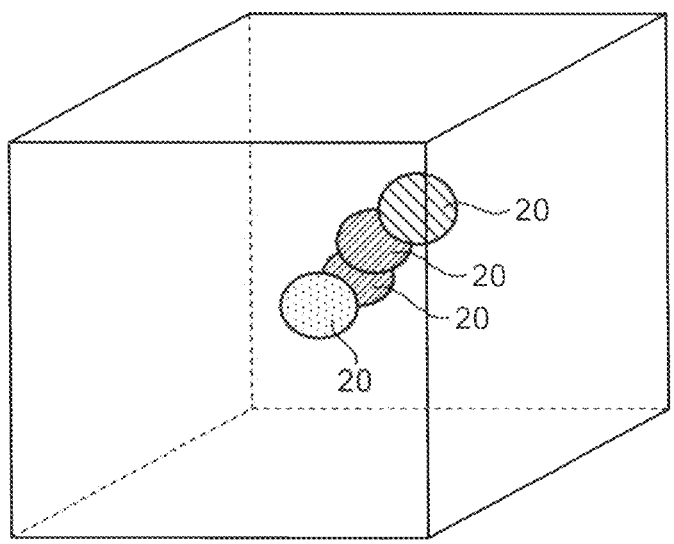
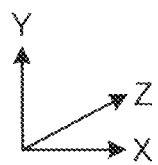

FIG.5
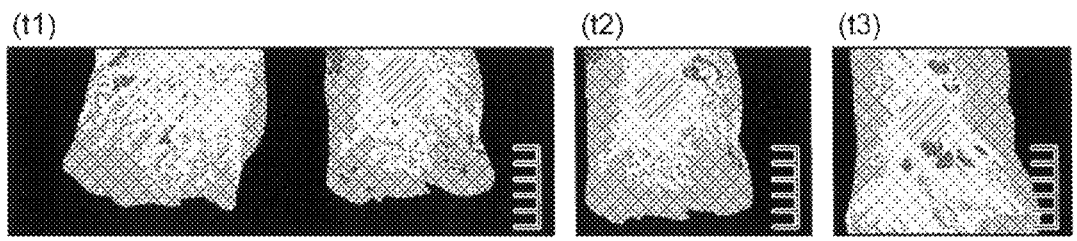
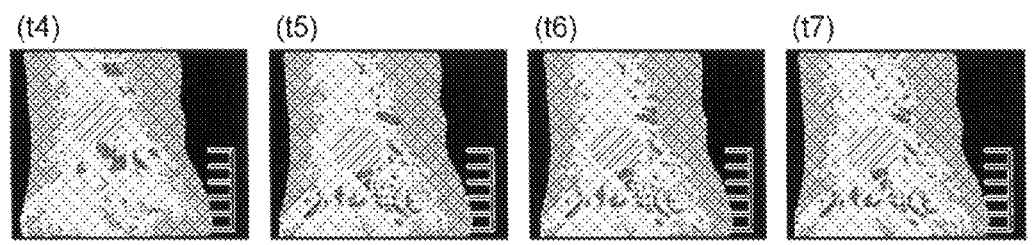
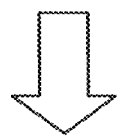
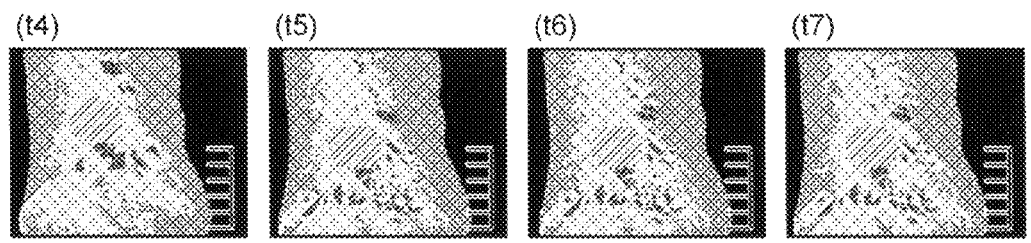

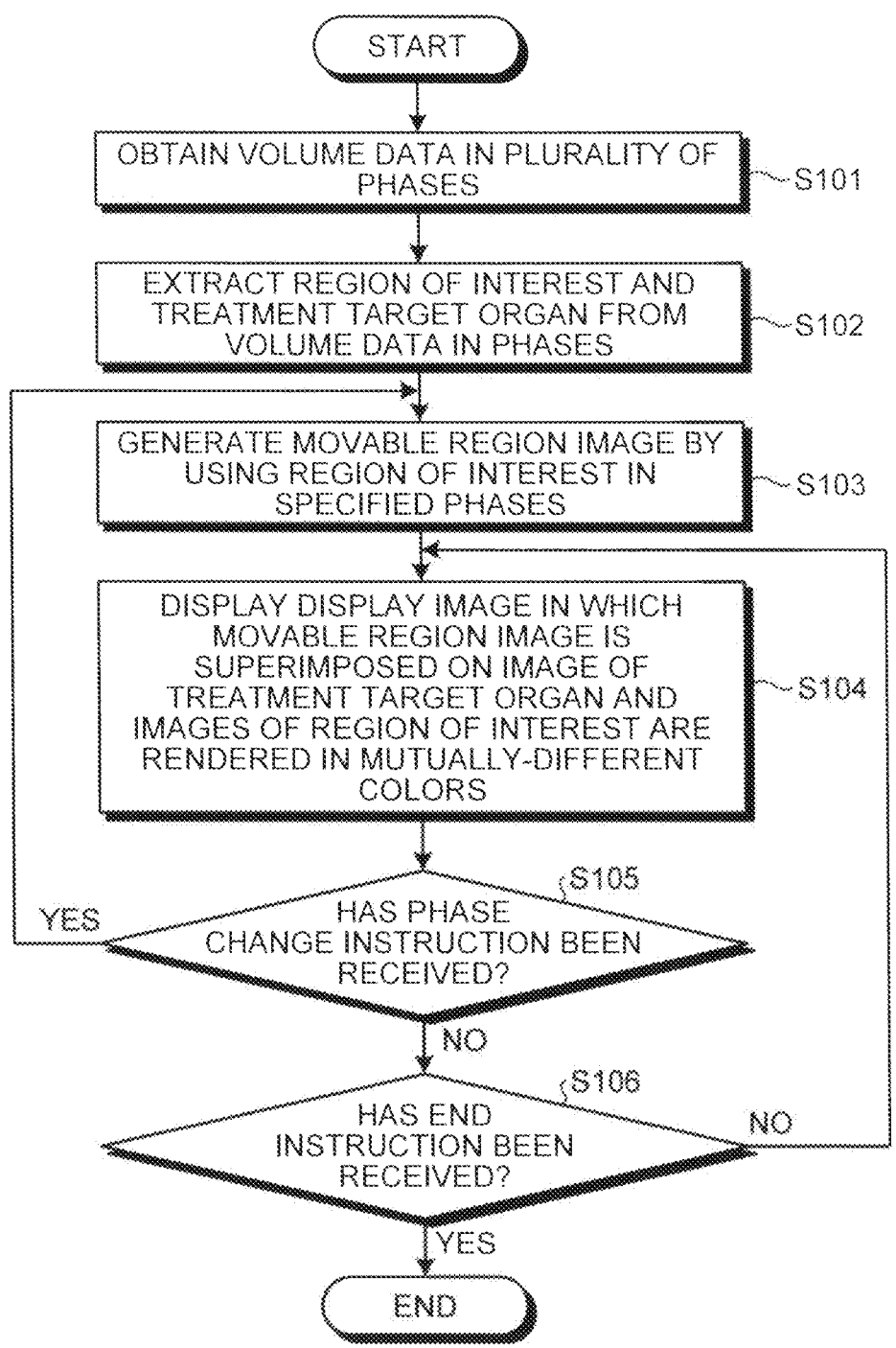

MEDICAL IMAGE PROCESSING APPARATUS AND RADIATION TREATMENT APPARATUS

CROSS-REFERENCE TO RELATED APPLICATIONS

This application is a continuation of International Application No. PCT/JP2013/073713, filed on Sep. 3, 2013 which claims the benefit of priority of the prior Japanese Patent Application No. 2012-193564, filed on Sep. 3, 2012 and Japanese Patent Application No. 2013-182609, filed on Sep. 3, 2013, the entire contents of which are incorporated herein by reference.

FIELD

Embodiments described herein relate generally to a medical image processing apparatus and a radiation treatment apparatus.

BACKGROUND

Conventionally, in radiation treatment planning, information about an Internal Target Volume (ITV) (i.e., a region in which a region of interest ("Clinical Target Volume [CTV]") such as a tumor can move around during a respiratory cycle) has been considered important in determining a region to which radiation is to be applied. It is desirable to arrange an ITV to be as small as possible, to reduce the burden on a patient.

As for methods for estimating an ITV, examples of known methods include a dynamic volume image taking process and a respiration synchronized image taking process that employ an X-ray Computed Tomography (CT) apparatus such as an Area Detector CT (ADCT) or a multi-row detector CT. During such an image taking process, it is possible to view movement states of a tumor at multiple points in time during a respiratory cycle, together with movements of structures that are present in the surroundings of the tumor. According to this conventional technique, however, it is not possible, in some situations, to make clear the relationship between the regions used for estimating the ITV and the respiratory states.

BRIEF DESCRIPTION OF THE DRAWINGS

FIG. 3 is a schematic drawing of an example of a process performed by an image generating unit according to the first embodiment;

FIG. 5 is a drawing for explaining an example of a phase selecting process performed by the extracting unit according to the first embodiment;

FIG. 7 is a flowchart of a procedure in a process performed by the medical image processing apparatus according to the first embodiment;

DETAILED DESCRIPTION

According to embodiment, a medical image processing apparatus comprising an extracting unit, a generating unit and a display controlling unit. The extracting unit that extracts a region of interest and an organ serving as a treatment target from each of a plurality of pieces of three-dimensional medical image data acquired chronologically. The generating unit that generates a movable region image in which each of images of the region of interest that correspond to a plurality of specified phases and that are among images of the region of interest extracted by the extracting unit from the plurality of pieces of three-dimensional medical image data is arranged in an extraction position in a three-dimensional coordinate system, while being characterized in such a manner that the phases are recognizable. The display controlling unit that causes a predetermined display unit to display a display image in which the movable region image during a treatment is superimposed, in a coordinate-corresponding manner, on an image showing the organ serving as the treatment target and corresponding to phases during the treatment.

Figure 1:
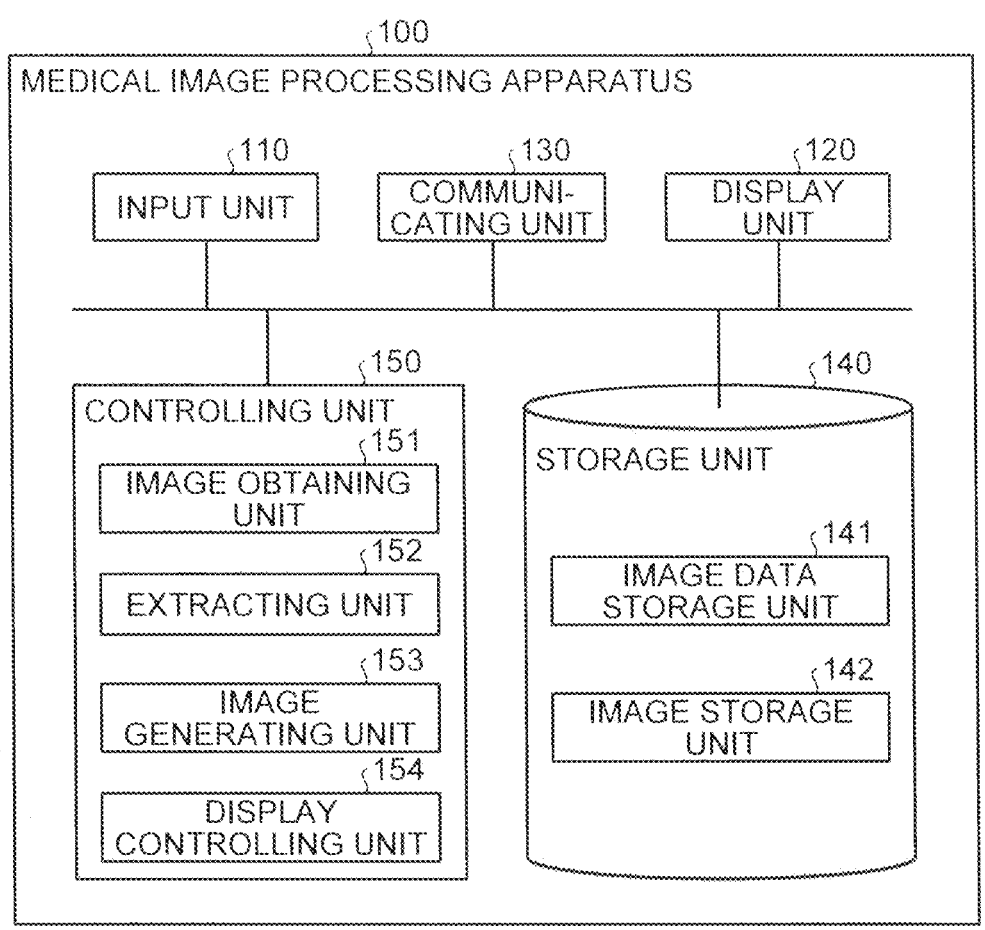
FIG. 1 is a diagram of an exemplary configuration of a medical image processing apparatus according to a first embodiment.

FIG. 1 is a diagram of an exemplary configuration of a medical image processing apparatus 100 according to a first embodiment. As illustrated in FIG. 1, the medical image processing apparatus 100 includes an input unit 110, a display unit 120, a communicating unit 130, a storage unit 140, and a controlling unit 150. For example, the medical image processing apparatus 100 may be configured with a workstation or an arbitrary personal computer and is connected to a medical image diagnosis apparatus, an image storing apparatus, and the like (not shown) via a network. The medical image diagnosis apparatus may be, for example, an X-ray Computed Tomography (CT) apparatus or a Magnetic Resonance Imaging (MRI) apparatus. Further, the medical image diagnosis apparatus is capable of generating three-dimensional medical image data (e.g., three-dimensional medical image data of images of a lung taken chronologically). The image storing apparatus is a database configured to store medical images therein. More specifically, the image storing apparatus stores the three-dimensional medical image data transmitted from the medical image diagnosis apparatus into a storage unit, so as to keep the three-dimensional medical image data stored therein. In the following sections, the three-dimensional medical image data may be referred to as "volume data".

The medical image processing apparatus 100, the medical image diagnosis apparatus, and the image storing apparatus described above are able to communicate with one another either directly or indirectly via, for example, an intra-hospital Local Area Network (LAN) installed in a hospital. For example, if a Picture Archiving and Communication System (PACS) has been introduced, the apparatuses transmit and receive medical images and the like to and from one another, according to the Digital Imaging and Communications in Medicine (DICOM) specifications.

The input unit 110 is configured with a mouse, a keyboard, a trackball and/or the like and is configured to receive inputs of various types of operations performed on the medical image processing apparatus 100 from an operator. More specifically, the input unit 110 receives an input of information for obtaining pieces of volume data that correspond to a plurality of phases and are used for estimating an ITV, from the image storing apparatus. For example, the input unit 110 receives an input for obtaining volume data of images of a lung taken chronologically through a dynamic scan performed by an X-ray CT apparatus, so as to use the obtained volume data for estimating the ITV. Further, the input unit 110 receives an input operation for specifying the plurality of phases used for estimating the ITV.

The display unit 120 is configured with a liquid display panel or the like that serves as a stereoscopic display monitor and is configured to display various types of information. More specifically, the display unit 120 displays a Graphical User Interface (GUI) used for receiving various types of operations from the operator, as well as a display image generated through a process performed by the controlling unit 150 (explained later), for example. The display image generated by the controlling unit 150 will be explained later. The communicating unit 130 is configured with a Network Interface Card (NIC) or the like and is configured to communicate with other apparatuses.

As illustrated in FIG. 1, the storage unit 140 includes an image data storage unit 141 and an image storage unit 142. For example, the storage unit 140 is configured with a hard disk, a semiconductor memory element, or the like and is configured to store therein various types of information. The image data storage unit 141 stores therein the volume data corresponding to the plurality of phases obtained from the image storing apparatus via the communicating unit 130. The image storage unit 142 stores therein, for example, image data that is currently being processed by the controlling unit 150 (explained later) and a movable region image generated through a process. The movable region image will be explained later.

The controlling unit 150 may be configured with an electronic circuit such as a Central Processing Unit (CPU) or a Micro Processing Unit (MPU) or an integrated circuit such as an Application Specific Integrated Circuit (ASIC) or a Field Programmable Gate Array (FPGA) and is configured to exercise overall control of the medical image processing apparatus 100.

Further, as illustrated in FIG. 1, the controlling unit 150 includes, for example, an image obtaining unit 151, an extracting unit 152, an image generating unit 153, and a display controlling unit 154. Further, the controlling unit 150 extracts a region of interest contained in each of the pieces of volume data that correspond to the plurality of phases and are used for estimating the ITV and further displays each of images of the region of interest corresponding to a plurality of specified phases, so as to be superimposed at corresponding coordinates on one image that shows an organ serving as a treatment target (hereinafter, "treatment target organ"). In the following sections, an example will be explained in which volume data of images of a tumor in a lung field taken chronologically by an X-ray CT apparatus is used as the pieces of volume data that correspond to the plurality of phases and are used for estimating the ITV.

The image obtaining unit 151 is configured to obtain the pieces of volume data that correspond to the plurality of phases and are used for estimating the ITV, from the image storing apparatus (not shown) and further stores the obtained pieces of volume data into the image data storage unit 141. For example, on the basis of information input by the operator via the input unit 110, the image obtaining unit 151 obtains the pieces of volume data of the images of the tumor in the lung field taken chronologically by the X-ray CT apparatus and further stores the obtained pieces of volume data into the image data storage unit 141.

The extracting unit 152 is configured to extract a region of interest and a treatment target organ from each of the plurality of pieces of volume data acquired chronologically. For example, the extracting unit 152 extracts a tumor as the region of interest from each of the plurality of pieces of volume data acquired in a plurality of phases during a respiratory cycle. Further, for example, the extracting unit 152 extracts a lung as the treatment target organ.

Figure 2A:
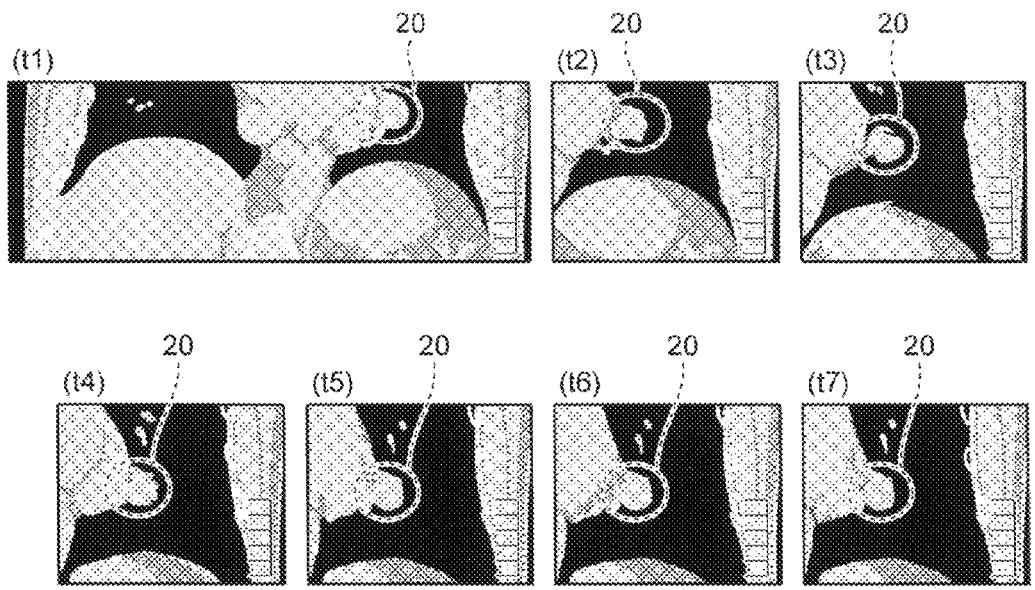
FIG. 2A is a drawing for explaining an example of a region of interest extracted by an extracting unit according to the first embodiment.

FIG. 2A is a drawing for explaining an example of a region of interest extracted by the extracting unit 152 according to the first embodiment. FIG. 2A illustrates CT images on a coronal plane generated from volume data corresponding to a plurality of phases; however, in actuality, the extracting unit 152 extracts a region of interest from each of the pieces of volume data from which (t1) to (t7) illustrated in FIG. 2A were generated. Further, (t1) to (t7) illustrated in FIG. 2A corresponding to the mutually-different phases represent pieces of data in a time-series order that were sequentially taken at times (t1) to (t7). In FIG. 2A, (t2) to (t7) each show only the region on the right-hand side of the CT image.

FIG. 2A illustrates the images obtained by performing fixed-point viewing on the pieces of volume data. In other words, FIG. 2A illustrates the CT images at predetermined coordinates in the volume data. For example, as illustrated in FIG. 2A, in the pieces of volume data corresponding to the plurality of phases, a tumor 20 shifts the position thereof along the lengthwise direction of the images, due to the respiration of the patient.

For example, as illustrated in FIG. 2A, the extracting unit 152 extracts the tumor 20 from each of the pieces of volume data (t1) to (t7) corresponding to the mutually-different phases. In other words, the extracting unit 152 extracts the coordinates of each of the voxels corresponding to the tumor 20 in the mutually-different phases (t1) to (t7), within the coordinate system of the volume data.

Figure 2B:
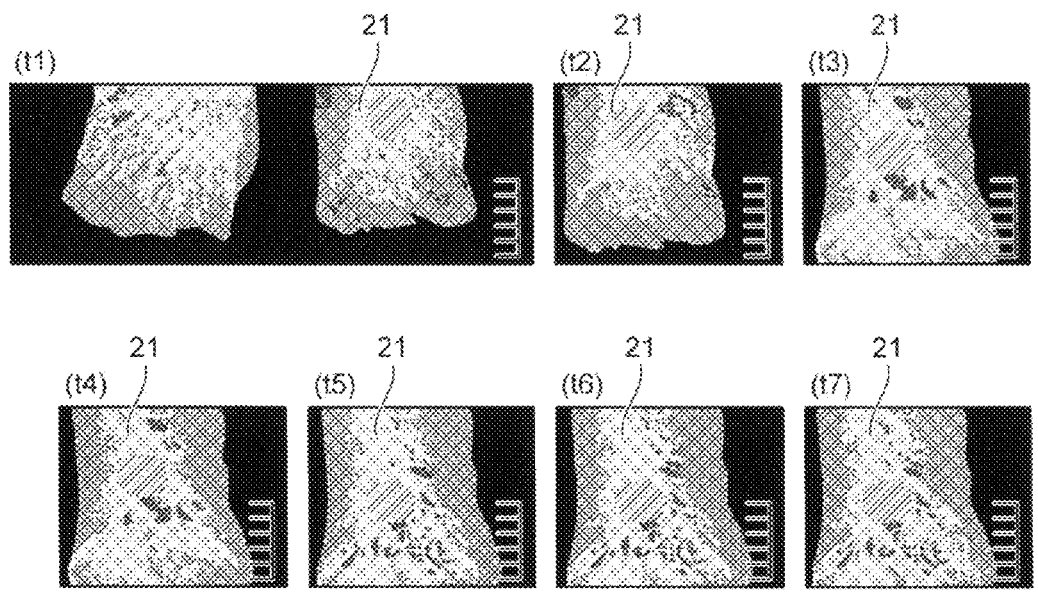
FIG. 2B is a drawing for explaining an example of an organ serving as a treatment target that is extracted by the extracting unit according to the first embodiment.

FIG. 2B is a drawing for explaining an example of an organ serving as a treatment target (a "treatment target organ") that is extracted by the extracting unit 152 according to the first embodiment. FIG. 2B illustrates Volume Rendering (VR) images each of which is generated from a different one of the pieces of volume data (t1) to (t7) illustrated in FIG. 2A; however, in actuality, the extracting unit 152 extracts the treatment target organ from each of the pieces of volume data from which (t1) to (t7) illustrated in FIG. 2B were generated. In FIG. 2B, (t2) to (t7) each show only the region on the right-hand side of the VR image. Further, in (t1) to (t7) illustrated in FIG. 2B, the region indicated with hatching represents the region of interest 20.

For example, as illustrated in FIG. 2B, the extracting unit 152 extracts a lung field 21 serving as a treatment target from each of the pieces of volume data (t1) to (t7) corresponding to the mutually-different phases. In other words, the extracting unit 152 extracts the coordinates of each of the voxels corresponding to the lung field 21 in the mutually-different phases (t1) to (t7), within the coordinate system of the volume data.

As for the region of interest (e.g., the tumor) and the treatment target organ (e.g., the lung field) described above, the extracting unit 152 extracts the region of interest (e.g., the tumor) and the treatment target organ (e.g., the lung field) by, for example, implementing a region growing method based on pixel values (voxel values) of the volume data. The region of interest and the treatment target organ are specified by the operator.

Returning to the description of FIG. 1, the image generating unit 153 is configured to generate a movable region image in which each of the images of the region of interest that correspond to a plurality of specified phases and that are among the images of the region of interest extracted by the extracting unit 152 from the plurality of pieces of volume data is arranged in an extraction position in a three-dimensional coordinate system, while being characterized in such a manner that the phases are recognizable. More specifically, the image generating unit 153 generates the movable region image in which each of the images of the region of interest that are in phases corresponding to predetermined respiratory states and that are among the images of the region of interest extracted from the plurality of pieces of volume data is arranged in the extraction position in the three-dimensional coordinate system, while being characterized in such a manner that the phases are recognizable.

For example, the image generating unit 153 generates the movable region image in which each of the tumor images extracted by the extracting unit 152 is arranged in the extraction position in the three-dimensional coordinate system, while being characterized in such a manner that the phases are recognizable. In this situation, the image generating unit 153 characterizes the images of the region of interest in such a manner that the phases are recognizable, by assigning mutually-different colors to the images of the region of interest corresponding to the plurality of specified phases. FIG. 3 is a schematic drawing of an example of a process performed by the image generating unit 153 according to the first embodiment. In this situation, the cube illustrated in FIG. 3 is virtual volume data having the same coordinate system as that of the volume data.

For example, as illustrated in FIG. 3, the image generating unit 153 generates the virtual volume data in which each of the images of the tumor 20 (hereinafter, "tumor images") that correspond to the phases specified by the operator and that are among the tumor images 20 extracted from the pieces of volume data corresponding to the mutually-different phases is arranged in a corresponding position in the coordinate system of the virtual volume data. Further, the image generating unit 153 generates a movable region image that indicates how the tumor 20 moves in the specified phases, by performing various types of processing processes on the generated virtual volume data. In this situation, the image generating unit 153 is able to generate the movable region image as a Multi-Planar Rendering (MPR) image, an oblique image, a VR image, or the like. Further, the image generating unit 153 is able to generate an MPR image, an oblique image, a VR image, or the like that renders a treatment target organ, by performing various types of processing processes not only on the virtual volume data described above, but also on volume data that corresponds to a plurality of phases and is obtained by the image obtaining unit 151.

Returning to the description of FIG. 1, the display controlling unit 154 is configured to cause the display unit 120 to display a display image in which a movable region image during a treatment is superimposed, in a coordinate-corresponding manner, on an image showing a treatment target organ and corresponding to phases during the treatment. More specifically, the display controlling unit 154 causes the display unit 120 to display the display image in which the movable region image is superimposed, in a coordinate-corresponding manner, on an MPR image, an oblique image, or a VR image showing the treatment target organ extracted by the extracting unit 152.

Figure 4A:
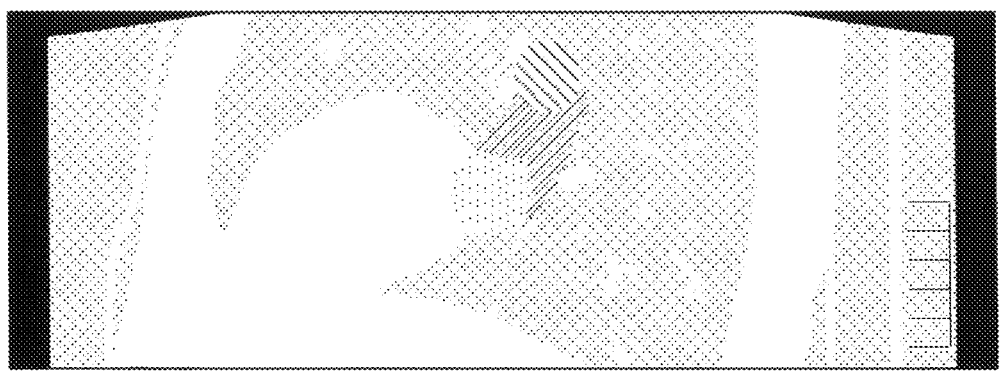
FIG. 4A is a drawing of an example of a display image displayed by a display controlling unit according to the first embodiment.
Figure 4B:
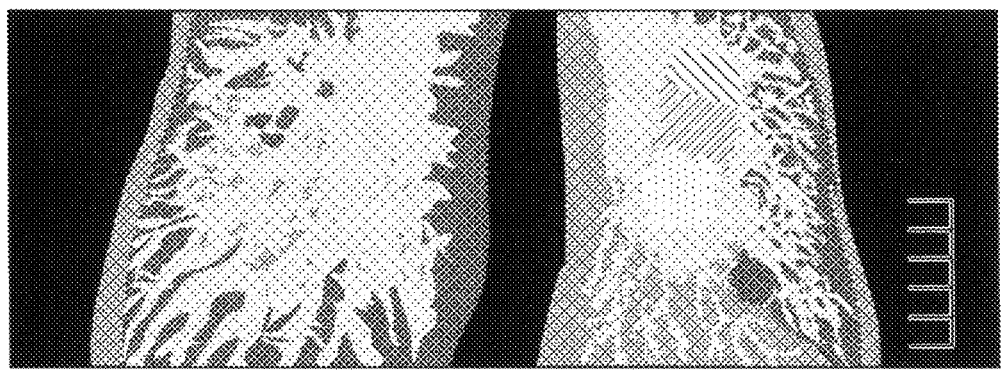
FIG. 4B is a drawing of another example of a display image displayed by the display controlling unit according to the first embodiment.

FIGS. 4A and 4B are drawings of examples of display images displayed by the display controlling unit 154 according to the first embodiment. FIG. 4A illustrates an MPR image, whereas FIG. 4B illustrates a VR image. For example, as illustrated in FIG. 4A, the display controlling unit 154 causes the display unit 120 to display a display image in which tumor images are superimposed on an MPR image (a two-dimensional[2D] image) of the lung field, while being rendered in mutually-different colors in correspondence with the mutually-different phases. Further, as illustrated in FIG. 4B, the display controlling unit 154 causes the display unit 120 to display a display image in which tumor images are superimposed on a VR image (a three-dimensional[3D] image) of the lung field, while being rendered in mutually-different colors in correspondence with the mutually-different phases. Because the movable regions of the region of interest (i.e., the tumor) rendered in the mutually-different colors in correspondence with the mutually-different phases are displayed in this manner while being superimposed on the image of the treatment target organ (i.e., the lung field), the viewer is able to recognize, at a glance, in what position the tumor is located in correspondence with the size of the lung field of the specific one of the lungs.

In this situation, the display controlling unit 154 is able to cause the images of the region of interest corresponding to the predetermined phases specified by the operator to be displayed in the mutually-different colors. In other words, the viewer is able to observe and conjecture movements of the region of interest corresponding to desired respiratory states. For example, the viewer is able to view a movable region of a region of interest corresponding to when the patient is taking a shallow breath or when the patient is taking a deep breath. In that situation, for example, the extracting unit 152 selects phases in which an image of the lung corresponding to a volume change in the shallow breath state was taken, on the basis of changes in the size (the volume) of the lung serving as the treatment target and further extracts the region of interest corresponding to the selected phases. After that, the image generating unit 153 generates a movable region image by using the extracted region of interest.

FIG. 5 is a drawing for explaining an example of the phase selecting process performed by the extracting unit 152 according to the first embodiment. For example, as illustrated in FIG. 5, the extracting unit 152 selects (t4) to (t7) as the phases corresponding to the shallow breath state (i.e., the changes in the volume of the lung are small) from among pieces of volume data corresponding to a plurality of phases and further generates a movable region image by using the region of interest (i.e., the tumor) extracted from each of the images in the selected phases (t4) to (t7). As a result, the viewer is able to observe, at a glance, how the tumor moves in correspondence with each of the respiratory states.

In this situation, the medical image processing apparatus 100 according to the first embodiment is also able to cause only such volume data images to be displayed that correspond to a specified respiratory state, by classifying the pieces of volume data in the plurality of phases obtained chronologically, according to the respiratory states thereof. For example, it is possible to classify the pieces of volume data according to "deep", "normal", and "shallow" respiratory states, so as to display one or more images on the basis of the classification. In that situation, at first, the input unit 110 receives an operation to specify a predetermined respiratory state. For example, the input unit 110 receives an operation to select one of the respiratory states desired by the user from among the three respiratory states "deep", "normal", and "shallow".

After that, the extracting unit 152 extracts pieces of three-dimensional medical image data in the phases corresponding to the predetermined respiratory state received by the input unit 110 and further extracts the region of interest and the treatment target organ from each of the extracted pieces of three-dimensional medical image data. For example, if the input unit 110 has received an operation to select the "shallow" respiratory state, the extracting unit 152 extracts pieces of volume data in the phases corresponding to the "shallow" respiratory state, from among the pieces of volume data corresponding to one respiratory cycle and further extracts the region of interest and the treatment target organ from each of the extracted pieces of volume data. In one example, when the input unit 110 has received an operation to select the "shallow" respiratory state, the extracting unit 152 extracts the pieces of volume data at (t4) to (t7) illustrated in FIG. 5. In this situation, the pieces of volume data in the phases corresponding to each respiratory state may be determined on the basis of the volume of the lung, or the correspondence relationship thereof may be stored in advance.

When the corresponding pieces of volume data are determined on the basis of the volume of the lung, for example, a range of volume change amount of the lung is set for each of the respiratory states. The extracting unit 152 then reads the range of volume change amount of the lung that is set in correspondence with the respiratory state received from the input unit 110. Further, the extracting unit 152 extracts pieces of volume data in which the volume change of the lung falls in the read range, as the pieces of volume data corresponding to the respiratory state received by the input unit 110. After that, the extracting unit 152 extracts a region of interest (e.g., a tumor) and a treatment target organ from each of the extracted pieces of volume data. Further, the image generating unit 153 generates a movable region image in which each of the images of the region of interest extracted by the extracting unit 152 is arranged in an extraction position in a three-dimensional coordinate system, while being characterized in such a manner that the phases are recognizable.

Further, the display controlling unit 154 is also able to cause the movable region of the tumor in each of the phases corresponding to an expiration period and to an inspiration period to be displayed as the display image. In that situation, on the basis of changes in the volume of the lung in the plurality of pieces of volume data extracted by the extracting unit 152, the image generating unit 153 generates a movable region image in which each of the tumor images in the phases corresponding to the expiration period and the inspiration period is arranged in an extraction position in the three-dimensional coordinate system, while being characterized in such a manner that the phases are recognizable.

More specifically, at first, the image generating unit 153 generates a volume change curve on the basis of the volume of the lung in each of the plurality of pieces of volume data. Further, by referring to the generated volume change curve, the image generating unit 153 determines phases corresponding to a period during which the volume decreases, as the phases corresponding to the expiration period and further generates a movable region image by using the tumor images extracted from these phases. Further, by referring to the generated volume change curve, the image generating unit 153 determines phases corresponding to a period during which the volume increases, as the phases corresponding to the inspiration period and further generates a movable region image by using the tumor images extracted from these phases. The display controlling unit 154 is thus able to provide the viewer with display images that indicate how the tumor moves in the expiration period and in the inspiration period, by superimposing each of the movable region images generated for the expiration period or for the inspiration period on an image of the lung field.

Figure 6A:
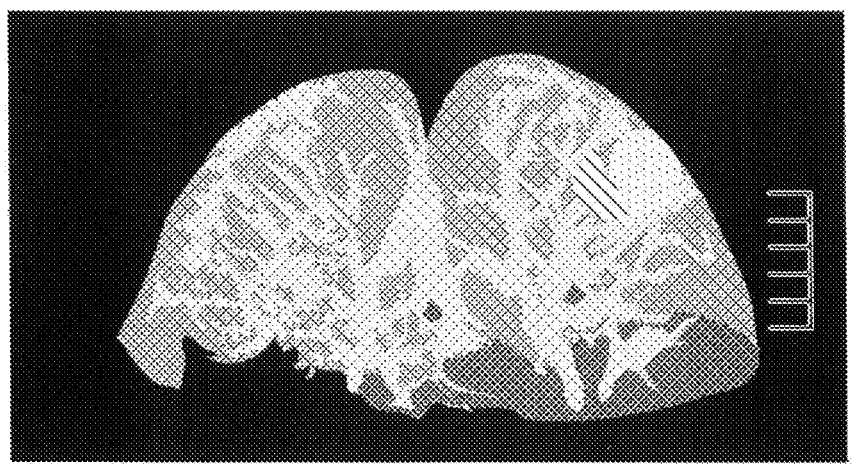
FIG. 6A is a drawing of display images for an expiration period and for an inspiration period displayed by the display controlling unit according to the first embodiment.
Figure 6B:
FIG. 6B is another drawing of the display images for the expiration period and for the inspiration period displayed by the display controlling unit according to the first embodiment.

FIGS. 6A and 6B are drawings of display images for an expiration period and for an inspiration period displayed by the display controlling unit 154 according to the first embodiment. FIG. 6A illustrates a display image showing a movable region of a tumor in an inspiration period, whereas FIG. 6B illustrates a display image showing a movable region of the tumor in an expiration period.

For example, as illustrated in FIG. 6A, the display controlling unit 154 causes the display unit 120 to display a display image in which the tumor images in the phases corresponding to an inspiration period are superimposed on a VR image of the lung field, while being rendered in mutually-different colors in correspondence with the mutually-different phases. Further, as illustrated in FIG. 6B, the display controlling unit 154 causes the display unit 120 to display a display image in which the tumor images in the phases corresponding to an expiration period are superimposed on a VR image of the lung field, while being rendered in mutually-different colors in correspondence with the mutually-different phases.

In the manner described above, the display controlling unit 154 is able to display each of the movable regions in the phases corresponding to the expiration period and to the inspiration period. Accordingly, the display controlling unit 154 is also able to further cause such a display image to be displayed that reflects the positions of the tumor in the phases corresponding to a maximum expiration and a maximum inspiration.

Further, the display controlling unit 154 is also able to cause the display unit 120 to display a display image in which an image showing a treatment target organ has been switched into the phases of the movable region image. For example, the display controlling unit 154 causes the display unit 120 to display a display image in which an image showing a lung has been switched into the phases of the movable region image. In an example, the display controlling unit 154 causes such a display image to be displayed in which a tumor image in the phase corresponding to the maximum expiration is superimposed on an image of the lung field corresponding to the maximum expiration. In another example, the display controlling unit 154 causes such a display image to be displayed in which a tumor image in the phase corresponding to the maximum inspiration is superimposed on an image of the lung field corresponding to the maximum inspiration.

FIG. 7 is a flowchart of a procedure in a process performed by the medical image processing apparatus 100 according to the first embodiment. As shown in FIG. 7, in the medical image processing apparatus 100 according to the first embodiment, the image obtaining unit 151 obtains pieces of volume data that are in a plurality of phases and are used for estimating an ITV (step S101). Further, the extracting unit 152 extracts a region of interest and a treatment target organ from each of the pieces of volume data in the mutually-different phases (step S102).

Subsequently, the image generating unit 153 generates a movable region image by using images of the region of interest corresponding to phases specified by the operator (step S103). Further, the display controlling unit 154 causes the display unit 120 to display a display image in which the movable region image is superimposed on an image of the treatment target organ extracted by the extracting unit 152 and in which the images of the region of interest are rendered in mutually-different colors in correspondence with the mutually-different phases (step S104).

After that, the image generating unit 153 judges whether an instruction has been received to change the phase of the region of interest to be displayed in the display image (step S105). In this situation, if an instruction to change the phase has been received (step S105: Yes), the image generating unit 153 returns to step S103 and generates a movable region image by using images of the region of interest in a newly-specified phase. On the contrary, if no instruction to change the phase has been received (step S105: No), the display controlling unit 154 judges whether an instruction to end the process of displaying the display image has been received (step S106).

In this situation, if no instruction to end the process has been received (step S106: No), the display controlling unit 154 returns to step S104 and causes the display unit 120 to continue displaying the display image. On the contrary, if an instruction to end the process has been received (step S106: Yes), the display controlling unit 154 ends the process of displaying the display image.

As explained above, according to the first embodiment, the extracting unit 152 extracts the region of interest (the tumor) and the treatment target organ (the lung field) from each of the plurality of pieces of volume data acquired chronologically. Further, the image generating unit 153 generates the movable region image in which each of the tumor images that correspond to the plurality of specified phases and that are among the tumor images extracted by the extracting unit 152 from the plurality of pieces of volume data is arranged in the extraction position in the three-dimensional coordinate system, while being characterized in such a manner that the phases are recognizable. After that, the display controlling unit 154 causes the display unit 120 to display the display image in which the movable region image is superimposed, in a coordinate-corresponding manner, on the image showing the lung field and having been extracted by the extracting unit 152. As a result, the medical image processing apparatus 100 according to the first embodiment makes it possible to make clear the relationship between the regions (the movable regions) used for estimating the ITV and the respiratory states (the phases).

The image generating unit 153 generates the movable region image in which each of the tumor images that are in the phases corresponding to the predetermined respiratory state and that are among the tumor images extracted from the plurality of pieces of volume data is arranged in the extraction position in the three-dimensional coordinate system, while being characterized in such a manner that the phases are recognizable. As a result, the medical image processing apparatus 100 according to the first embodiment makes it possible to make clear the relationship between the various respiratory states and the movable regions of the tumor.

Further, according to the first embodiment, the input unit 110 receives the operation to specify the predetermined respiratory state. After that, the extracting unit 152 extracts the pieces of volume data in the phases corresponding to the predetermined respiratory state received by the input unit 110 and further extracts the region of interest and the treatment target organ from each of the extracted pieces of volume data. Further, the image generating unit 153 generates the movable region image in which each of the images of the region of interest extracted by the extracting unit 152 is arranged in the extraction position in the three-dimensional coordinate system, while being characterized in such a manner that the phases are recognizable. As a result, the medical image processing apparatus 100 according to the first embodiment is able to read all of the pieces of volume data in the phases corresponding to the respiratory state desired by the user and to cause the images thereof to be displayed. The medical image processing apparatus 100 according to the first embodiment thus makes it easier to analyze the relationship between the various respiratory states and the movable regions of the tumor.

Further, according to the first embodiment, the extracting unit 152 extracts the tumor from each of the plurality of pieces of volume data acquired in the plurality of phases during the respiratory cycle. Further, the image generating unit 153 generates the movable region image in which each of the tumor images extracted by the extracting unit 152 is arranged in the extraction position in the three-dimensional coordinate system, while being characterized in such a manner that the phases are recognizable. After that, the display controlling unit 154 causes the display unit 120 to display the display image in which the movable region image is superimposed, in a coordinate-corresponding manner, on the MPR image, the oblique image, or the VR image showing the lung field serving as the treatment target. As a result, the medical image processing apparatus 100 according to the first embodiment makes it possible to view the display image in a 2D or 3D manner.

Further, according to the first embodiment, the image generating unit 153 generates the movable region image in which each of the tumor images that are in the phases corresponding to the expiration period and the inspiration period and that are among the tumor images extracted from the plurality of pieces of volume data is arranged in the extraction position in the three-dimensional coordinate system, while being characterized in such a manner that the phases are recognizable. As a result, the medical image processing apparatus 100 according to the first embodiment makes it possible to indicate the movable regions of the tumor for the expiration period and for the inspiration period, which are among various respiratory states.

Further, according to the first embodiment, the image generating unit characterizes the tumor images in such a manner that the phases are recognizable, by assigning the mutually-different colors to the tumor images corresponding to the plurality of specified phases. As a result, the medical image processing apparatus 100 according to the first embodiment makes it possible to provide the viewer with the display image from which the relationship between the movable regions and the respiratory states is observed at a glance.

Further, according to the first embodiment, the display controlling unit 154 causes the display unit 120 to display the display image in which the image showing the lung field serving as the treatment target has been switched into the phases of the movable region image. As a result, the medical image processing apparatus 100 according to the first embodiment makes it possible for the viewer to definitely recognize how the movable region changes in correspondence with each of the various states of the lung field.

Further, according to the first embodiment, the extracting unit 152 extracts the lung as the treatment target organ. Further, on the basis of the changes in the volume of the lung in the plurality of pieces of volume data extracted by the extracting unit 152, the image generating unit 153 generates the movable region image in which the tumor images in the phases corresponding to the maximum expiration and the maximum inspiration are arranged in the extraction positions in the three-dimensional coordinate system, while being characterized in such a manner that the phases are recognizable. Further, the display controlling unit 154 causes the display unit 120 to display the display image in which the image showing the lung has been switched into the phases of the movable region image. As a result, the medical image processing apparatus 100 according to the first embodiment is able to display the positions of the tumor at the point in time when the lung has a maximum size and at the point in time when the lung has a minimum size. Thus, the medical image processing apparatus 100 according to the first embodiment makes it possible to clearly indicate how much the tumor moves at maximum.

In the first embodiment above, the example is explained in which the medical image processing apparatus displays the movable regions of the tumor. In a second embodiment, a radiation treatment apparatus provided with the medical image processing apparatus 100 illustrated in FIG. 1 will be explained.

Figure 8:
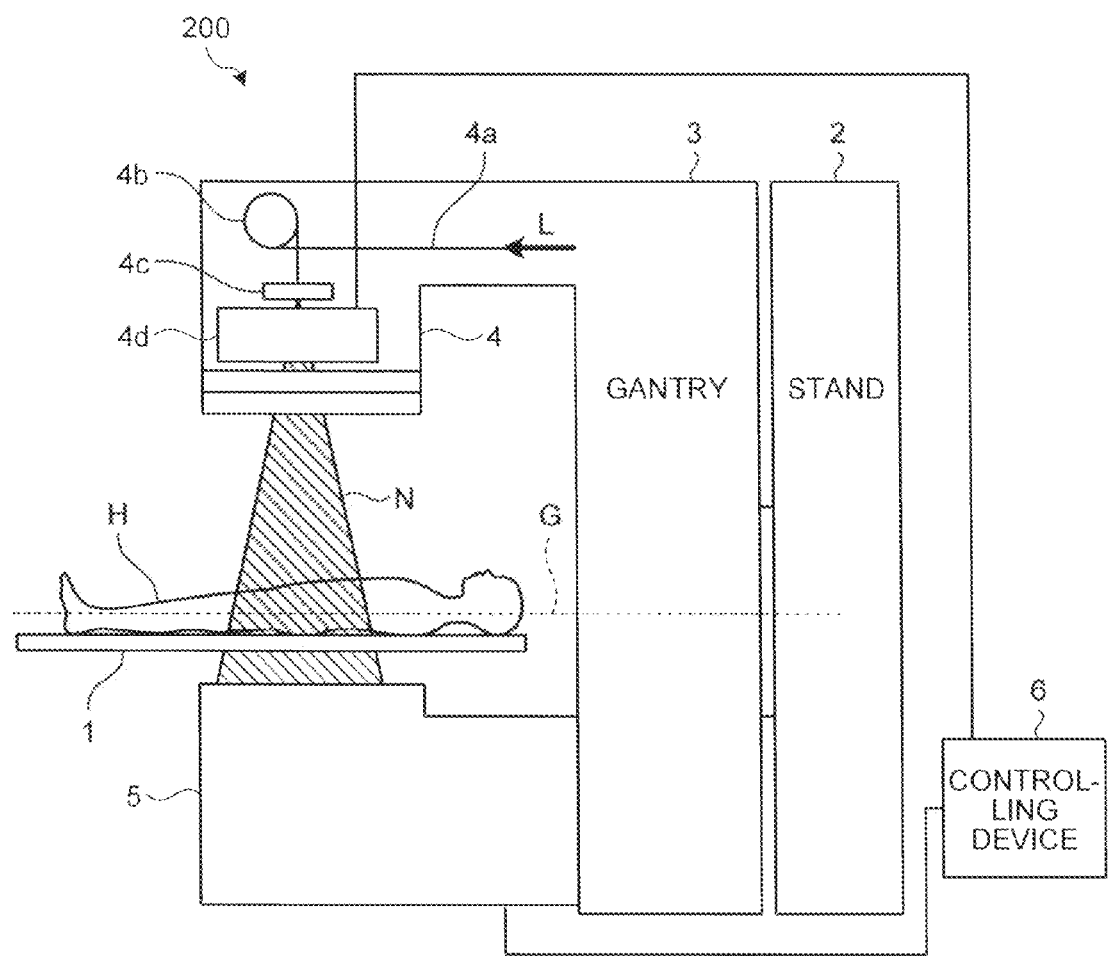
FIG. 8 is a diagram of an exemplary configuration of a radiation treatment apparatus according to a second embodiment.

FIG. 8 is a diagram of an exemplary configuration of a radiation treatment apparatus 200 according to the second embodiment. As illustrated in FIG. 8, the radiation treatment apparatus 200 according to the second embodiment includes a couchtop 1, a stand 2, a gantry 3, a treatment head 4, a radiation fluoroscopy unit 5, and a controlling device 6.

The couchtop 1 is of a couch on which an examined subject (hereinafter, a "patient") H who is subject to radiation treatment is placed. The stand 2 is configured to support the gantry 3 and has, on the inside thereof, a driving device for causing the gantry 3 to rotate. The gantry 3 is configured to support the treatment head 4 and the radiation fluoroscopy unit 5 so as to face each other while the couchtop 1 is interposed therebetween. The gantry 3 moves the treatment head 4 and the radiation fluoroscopy unit 5 centered about an axis G that extends along the horizontal direction in which the patient H is positioned. Further, the gantry 3 has, on the inside thereof, an electron gun, a waveguide element, and the like (not shown).

The treatment head 4 is configured to generate a treatment-purpose radiation beam used for the treatment of the patient H. More specifically, the treatment head 4 has, on the inside thereof, a waveguide element 4a, a bending magnet 4b, a target 4c, and a collimator 4d. Further, an electron beam L generated by the electron gun included in the gantry 3 becomes incident to the bending magnet 4b, after being accelerated by the waveguide element 4a. The bending magnet 4b causes the electron beam L, which has become incident thereto, to collide with the target 4c by directing the electron beam L downward. As a result, a treatment-purpose radiation beam N is generated. The generated treatment-purpose radiation beam N is applied to the patient H, after the form of radiation and the radiation dose distribution are adjusted by the collimator 4d.

The radiation fluoroscopy unit 5 is configured to detect the radiation beams that have passed through the patient H and to take a fluoroscopic image used for facilitating positioning of the patient H and/or re-confirmation of the region of an affected site. The controlling device 6 is configured to control the entirety of the radiation treatment apparatus 200. For example, the controlling device 6 causes the gantry 3 to rotate by driving the driving device included in the stand 2, in accordance with an instruction from the operator. Further, for example, the controlling device 6 applies a predetermined image processing process on an image taken by a camera included in the radiation fluoroscopy unit 5 and displays the image resulting from the image processing process.

The radiation treatment apparatus 200 according to the second embodiment configured as described above determines a region to which the radiation is to be applied, on the basis of the movable regions of the tumor calculated by the medical image processing apparatus 100 illustrated in FIG. 1. For example, the controlling device 6 includes the controlling unit 150 illustrated in FIG. 1, so as to set an ITV on the basis of the movable regions of a region of interest derived by the controlling unit 150. Further, the controlling device 6 applies the treatment-purpose radiation beam to the ITV that was set.

As explained above, the radiation treatment apparatus 200 according to the second embodiment determines the ITV on the basis of the movable regions of the tumor calculated by the medical image processing apparatus 100 and applies the treatment-purpose radiation beam to the determined ITV. As a result, the radiation treatment apparatus 200 according to the second embodiment is able to keep the ITV small and to reduce the size of the region to which the treatment-purpose radiation beam is applied. Thus, the radiation treatment apparatus 200 according to the second embodiment makes it possible to reduce the burden on the patient.

The first and the second embodiments have thus been explained. The disclosure herein, however, may be embodied in various modes other than those described in the first and the second embodiments.

In the first embodiment above, the example is explained in which the movable region image is generated in which the images are arranged in the extraction positions in the three-dimensional coordinate system while being characterized in such a manner that the phases are recognizable, so that the display unit 120 is caused to display the display image in which the movable region image is superimposed, in the coordinate-corresponding manner, on the image showing the lung field. However, possible embodiments are not limited to this example. It is also acceptable to perform a simulation by using the technique disclosed herein.

Figure 9A:
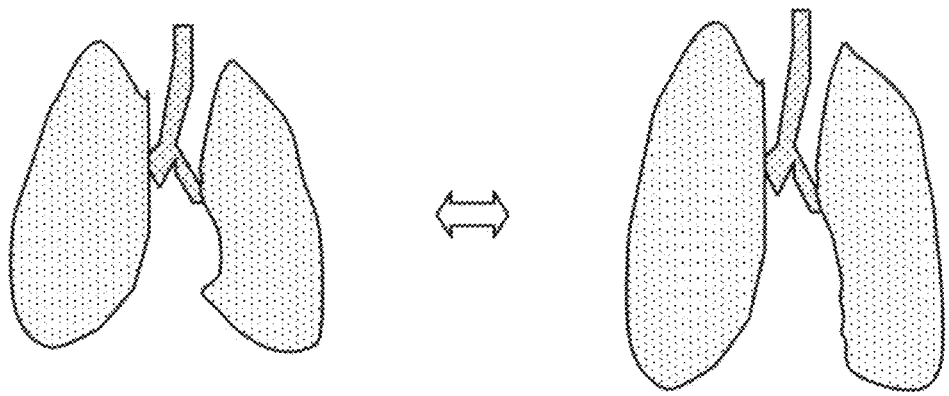
FIG. 9A is a drawing for explaining an example of a simulation according to a third embodiment.
Figure 9B:
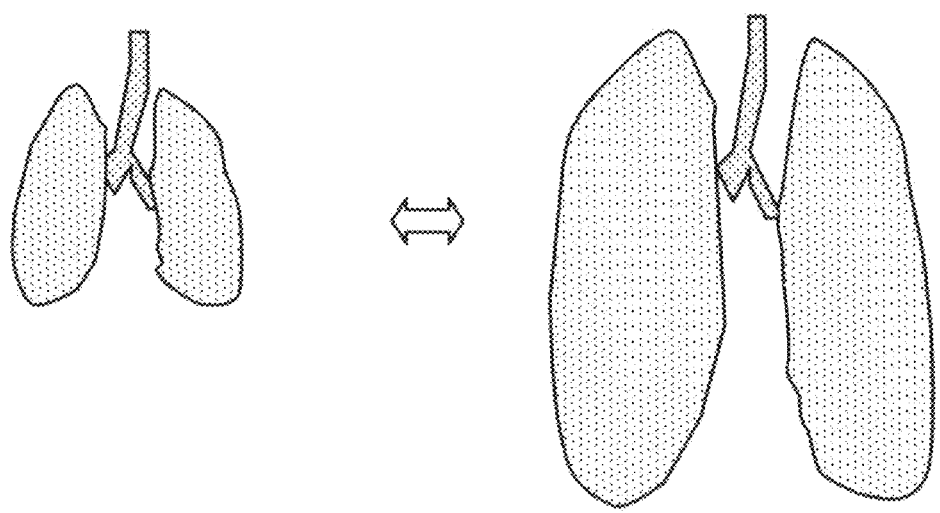
FIG. 9B is another drawing for explaining the example of the simulation according to the third embodiment.
Figure 9C:
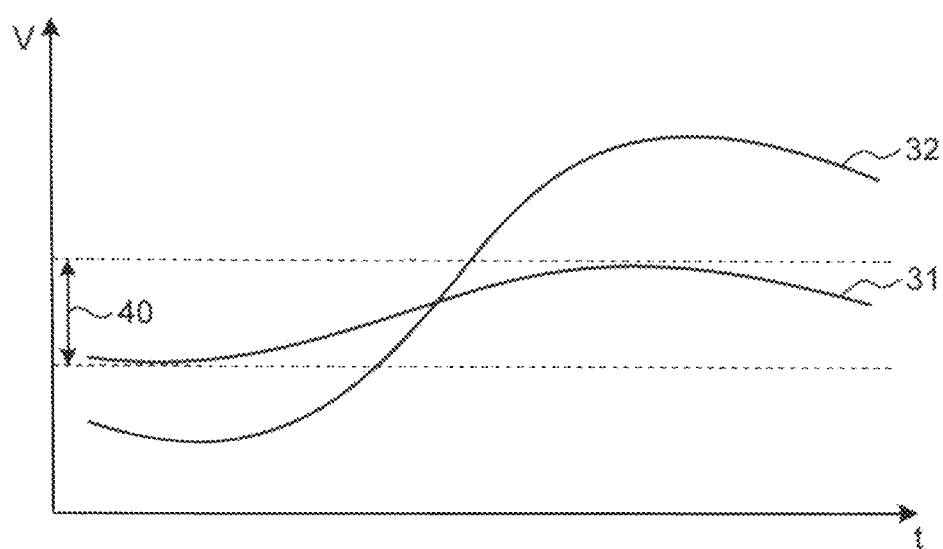
FIG. 9C is yet another drawing for explaining the example of the simulation according to the third embodiment.

FIGS. 9A to 9C are drawings for explaining an example of a simulation according to a third embodiment. FIGS. 9A to 9C illustrate an example in which movable regions are simulated in various respiratory states. FIGS. 9A and 9B illustrate changes in the volume of the lung field in mutually-different respiratory states. FIG. 9C is a chart of the changes in the volume of the lung field in mutually-different respiratory states, and the vertical axis expresses the volume, whereas the horizontal axis expresses time.

For example, during a treatment, because the patient is breathing at rest, the changes in the volume of the lung field of the patient are small, as illustrated in FIG. 9A. In contrast, during a medical examination, because the patient is breathing with deep inspirations and deep expirations, the changes in the volume of the lung field of the patient are large, as illustrated in FIG. 9B. In other words, as illustrated with a curve 31 in FIG. 9C, the volume of the lung field of the patient breathing at rest does not exhibit significant changes during the one respiratory cycle. However, as illustrated with a curve 32 in FIG. 9C, the volume of the lung field of the patient taking a deep breath exhibits significant changes during the one respiratory cycle.

Accordingly, the movements of the region of interest during one respiratory cycle are different between when the patient is breathing at rest and when the patient is taking a deep breath. For example, the position of the region of interest in a three-dimensional coordinate system at a maximum inspiration while the patient is breathing at rest is significantly different from the position of the region of interest in the three-dimensional coordinate system at a maximum inspiration while the patient is taking a deep breath. In other words, if a movable region image of a region of interest (e.g., a tumor) is generated by using data during a medical examination (i.e., data acquired while the patient is breathing at rest) and is superimposed on an image acquired during a treatment on the basis of the timing of the respiration, there is a possibility that the region of interest may be superimposed on a part where the lung field is not present.

To cope with this situation, the medical image processing apparatus 100 according to the third embodiment analyzes the respiratory state of the patient during a treatment (i.e., how much the lung field changes in size during one respiratory cycle) on the basis of images. Further, the medical image processing apparatus 100 simulates the position of the region of interest corresponding to the analyzed respiratory state by using data acquired during a medical examination. For example, as illustrated in FIG. 9C, the controlling unit 150 analyzes a range 40 of changes in the volume of the lung field while the patient is breathing at rest, on the basis of the data represented by the curve 31. The display controlling unit 154 obtains data of the positions of the region of interest corresponding to the volumes contained in the range 40 analyzed by the controlling unit 150, from the data represented by the curve 32.

More specifically, the display controlling unit 154 simulates each of the positions of the region of interest in a three-dimensional coordinate system corresponding to the volumes represented by the curve 31, on the basis of the positions of the region of interest with the corresponding volumes represented by the curve 32. In other words, the medical image processing apparatus 100 according to the third embodiment generates and displays a display image that is brought into correspondence on the basis of the sizes of the treatment target organ, instead of on the basis of the respiratory timing. As explained above, the medical image processing apparatus 100 according to the third embodiment is able to simulate the positions of the region of interest and the sizes of the organ, on the basis of the image at the beginning (e.g., the image acquired during a medical examination).

Further, when the positions of the region of interest have been simulated as explained above, another arrangement is also acceptable in which a region where the region of interest is expected to be present is displayed within a treatment target region. For example, the display controlling unit 154 may calculate a region where the extracted region of interest has a high probability of being present by using information about respiratory cycles and may exercise control so as to cause the calculated region to be displayed together as a movable region image.

In the first and the second embodiments described above, the examples are explained in which the depths of the breathing are used as the phases; however, possible embodiments are not limited to these examples. For instance, pulsation states may be used as the phases.

In the first embodiment described above, the example using the CT images is explained; however, possible embodiments are not limited to this example. For instance, Magnetic Resonance (MR) images or the like may be used.

In the first embodiment described above, the example is explained in which the image obtaining unit 151 obtains the volume data from either the image storing apparatus or the medical image diagnosis apparatus; however, possible embodiments are not limited to this example. For instance, a medical doctor may carry the volume data in a portable storage medium such as a flash memory or an external hard disk and may store the volume data into the image data storage unit 141 of the medical image processing apparatus 100. In that situation, the image obtaining unit 151 does not need to perform the volume data obtaining process.

Further, in the first embodiment described above, the medical image processing apparatus 100 is explained; however, possible embodiments are not limited to this example. For instance, the storage unit 140 and the controlling unit 150 that are included in the medical image processing apparatus 100 in FIG. 1 may be incorporated in a medical image diagnosis apparatus so that the processes described above are executed by the medical image diagnosis apparatus.

By using the medical image processing apparatus according to at least one aspect of the embodiments described above, it is possible to make clear the relationship between the regions used for estimating the ITV and the respiratory states.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry having an
an extracting unit that extracts a region of interest and an organ serving as a treatment target from each of a plurality of pieces of three-dimensional medical image data acquired chronologically;
a generating unit that generates a movable region image in which each of images of the region of interest that correspond to a plurality of specified phases and that are among images of the region of interest extracted by the extracting unit from the plurality of pieces of three-dimensional medical image data is arranged in an extraction position in a three-dimensional coordinate system, while being characterized in such a manner that the phases are recognizable; and
a display controlling unit that causes a predetermined display unit to display a display image in which the movable region image during a treatment is superimposed, in a coordinate-corresponding manner, on an image showing the organ serving as the treatment target and corresponding to phases during the treatment.

2. The medical image processing apparatus according to claim 1, wherein the generating unit generates the movable region image in which each of the images of the region of interest that are in the phases corresponding to a respiratory state during the treatment and that are among the images of the region of interest extracted from the plurality of pieces of three-dimensional medical image data is arranged in the extraction position in the three-dimensional coordinate system, while being characterized in such a manner that the phases are recognizable.

3. The medical image processing apparatus according to claim 2, further comprising: a receiver that receives an operation to specify the respiratory state, wherein
the extracting unit extracts pieces of three-dimensional medical image data in phases corresponding to the predetermined respiratory state received by the receiver and further extracts the region of interest and the organ serving as the treatment target that correspond, from each of the extracted pieces of three-dimensional medical image data, and
the generating unit generates the movable region image in which each of the images of the region of interest extracted by the extracting unit is arranged in the extraction position in the three-dimensional coordinate system, while being characterized in such a manner that the phases are recognizable.

4. The medical image processing apparatus according to claim 2, wherein the display controlling unit calculates a region where the extracted region of interest has a high probability of being present, by using information about respiratory cycles and exercises control so as to cause the calculated region to be displayed together as the movable region image.

5. The medical image processing apparatus according to claim 2, wherein the generating unit generates the movable region image in which each of images of the region of interest that are in phases corresponding to an expiration period and an inspiration period and that are among the images of the region of interest extracted from the plurality of pieces of three-dimensional medical image data is arranged in the extraction position in the three-dimensional coordinate system, while being characterized in such a manner that the phases are recognizable.

6. The medical image processing apparatus according to claim 1, wherein
the extracting unit extracts a tumor as the region of interest from each of the plurality of pieces of three-dimensional medical image data acquired in a plurality of phases during a respiratory cycle,
the generating unit generates the movable region image in which each of images of the tumor extracted by the extracting unit is arranged in the extraction position in the three-dimensional coordinate system, while being characterized in such a manner that the phases are recognizable, and
the display controlling unit causes the predetermined display unit to display the display image in which the movable region image during the treatment is superimposed, in a coordinate-corresponding manner, on a Multi-Planar Rendering (MPR) image, an oblique image, or a Volume Rendering (VR) image showing the organ serving as the treatment target and corresponding to the phases during the treatment.

7. The medical image processing apparatus according to claim 6, wherein
the extracting unit extracts a lung as the organ serving as the treatment target,
on a basis of changes in a volume of the lung in the plurality of pieces of three-dimensional medical image data extracted by the extracting unit, the generating unit generates the movable region image in which images of the tumor in phases corresponding to a maximum expiration and a maximum inspiration are arranged in extraction positions in the three-dimensional coordinate system, while being characterized in such a manner that the phases are recognizable, and
the display controlling unit causes the predetermined display unit to display the display image in which the image showing the lung has been switched into the phases of the movable region image during the treatment.

8. The medical image processing apparatus according to claim 1, wherein the generating unit characterizes the images of the region of interest in such a manner that the phases are recognizable, by assigning mutually-different colors to the images of the region of interest corresponding to the plurality of specified phases.

9. The medical image processing apparatus according to claim 1, wherein the display controlling unit causes the predetermined display unit to display the display image in which the image showing the organ serving as the treatment target and corresponding to the phases during the treatment has been switched into the phases of the movable region image during the treatment.

10. A radiation treatment apparatus comprising:
the medical image processing apparatus according to claim 1; and
a controlling unit that determines a region to which radiation is to be applied, on a basis of a movable region of a tumor calculated by the medical image processing apparatus.

* * * * *